(12) United States Patent
Holmes

(10) Patent No.: US 8,341,846 B1
(45) Date of Patent: Jan. 1, 2013

(54) HAIR CLIPPERS WITH ELECTRICALLY ADJUSTABLE BLADES

(76) Inventor: Lonnie Holmes, Bellport, NY (US)

( * ) Notice: Subject to any disclaimer, the term of this patent is extended or adjusted under 35 U.S.C. 154(b) by 359 days.

(21) Appl. No.: 12/592,537

(22) Filed: Nov. 24, 2009

Related U.S. Application Data

(60) Provisional application No. 61/117,434, filed on Nov. 24, 2008.

(51) Int. Cl.
*B26B 19/02* (2006.01)
*B26B 19/28* (2006.01)
*B26B 19/38* (2006.01)

(52) U.S. Cl. ............... 30/43.1; 30/200; 30/201; 30/202; 30/208; 30/209; 30/210

(58) Field of Classification Search .................. 30/43.1, 30/200–202, 223, 224, 208–210
See application file for complete search history.

(56) References Cited

U.S. PATENT DOCUMENTS

| | | | |
|---|---|---|---|
| 296,759 A | 4/1884 | Lacasse | |
| 1,516,635 A * | 11/1924 | Friedman | 30/202 |
| 1,774,046 A | 8/1930 | Wahl | |
| 2,214,501 A | 9/1940 | Kinkead | |
| 2,345,263 A | 3/1944 | Jepson | |
| 2,677,178 A * | 5/1954 | Daggett | 30/202 |
| 2,726,447 A * | 12/1955 | Maloy | 30/202 |
| 3,287,805 A * | 11/1966 | Du Charme | 30/202 |
| 3,295,201 A | 1/1967 | Pucino | |
| 3,431,643 A * | 3/1969 | Miceli | 30/42 |
| 3,659,180 A * | 4/1972 | Urbush | 320/DIG. 21 |
| 3,694,916 A | 10/1972 | Harms | |
| 4,085,503 A | 4/1978 | Beck | |
| 4,571,830 A | 2/1986 | Kassner | |
| 4,989,324 A | 2/1991 | Andis | |
| 5,367,772 A | 11/1994 | Ogawa | |
| 6,276,060 B1 | 8/2001 | Faulstich | |
| 6,578,269 B2 | 6/2003 | Wilcox | |
| 6,665,938 B2 | 12/2003 | McCambridge | |
| 6,742,262 B2 | 6/2004 | Rizzuto, Jr. | |
| 7,080,458 B2 | 7/2006 | Andis | |
| 7,100,286 B2 | 9/2006 | Nakakura | |
| 7,234,242 B2 * | 6/2007 | Yao | 30/201 |
| 7,509,743 B2 * | 3/2009 | Oh | 30/201 |
| 7,992,303 B2 * | 8/2011 | Liao | 30/43.1 |

(Continued)

OTHER PUBLICATIONS

Micro Servo, Electromechanical Components Department, Hobby Engineering, www.hobbyengineering.com.
Shigetoshi Sakon, Tadashi Hamada, Shinji Fujimoto, Norimasa Umesaki, and Akira Kobayashi, Surface modification of electric hair clipper blade for increasing its lifetime, ScienceDirect, www.sciencedirect.com, available online Apr. 7, 2008, vol. 83, Issue 1, Sep. 4, 2008, pp. 119-123.

(Continued)

*Primary Examiner* — Jason Daniel Prone
(74) *Attorney, Agent, or Firm* — Alfred M. Walker

(57) ABSTRACT

The hair clippers use a self-contained motor-driven adjustment mechanism to adjust the relative position of the stationary and reciprocating blades of a common type of blade set. Two momentary switches operable by the thumb of the hand holding the clipper afford a barber total automatic adjustment with the clipper itself in an on or off condition. Since the small gear motors used for the adjustment are brush type or brushless permanent magnet motors which are operated by direct current, the adjustment feature is most compatible with cordless clippers already using an on-board DC source in the form of a re-chargeable battery to drive the reciprocating blade. The invention will be described as a modification of a cordless clipper, although AC driven corded type clippers can also be modified with this feature by the addition of an on-board AC to DC power supply for the adjustment motor.

10 Claims, 7 Drawing Sheets

U.S. PATENT DOCUMENTS

| | | | |
|---|---|---|---|
| 7,992,307 B2 * | 8/2011 | Smal | 30/202 |
| 2005/0011076 A1 * | 1/2005 | Andis | 30/223 |
| 2005/0223560 A1 | 10/2005 | Walls | |
| 2008/0201955 A1 | 8/2008 | Leung | |
| 2008/0289184 A1 * | 11/2008 | Williams | 30/200 |

OTHER PUBLICATIONS

About Wahl, Wahl Home Products, http://consumer.wahl.com/about.cfm.

* cited by examiner

HAIR CLIPPERS WITH ELECTRICALLY ADJUSTABLE BLADES

RELATED APPLICATIONS

This application is based upon provisional application Ser. No. 61/117,434 filed Nov. 24, 2008, which application is incorporated by reference herein. Applicant claims priority under 35 USC §119(e) therefrom.

FIELD OF THE INVENTION

The present invention relates to hair cutting.

BACKGROUND OF THE INVENTION

Electrically operated hair clippers have been used for many years. Some of the commonly available models have a manual lever on the side to incrementally adjust the relative position between the stationary and the reciprocating blades in a blade set to adjust the minimum length of hair that is being clipped. Other prior art patents show infinite adjustability over a range. The prior art does not reveal motor-powered continuous adjustability of the blade set which affords the barber the ability to perform the adjustment even during the clipping activity by simply activating a switch.

OBJECTS OF THE INVENTION

It is therefore an object of the present invention to provide a hair clippers device with infinitely variable blade distances from the scalp of the patron.

Other objects which become apparent from the following description of the present invention.

SUMMARY OF THE INVENTION

The hair clippers of this invention use a self-contained motor-driven adjustment mechanism to adjust the relative position of the stationary and reciprocating blades of a common type of blade set. Two momentary switches operable by the thumb of the hand holding the clipper afford a barber total automatic adjustment with the clipper itself in an on or off condition. There is no need for two-handed fidgeting or selection of only a few discrete increments of length adjustment as with the commonly available models. Since the small gear motors used for the adjustment are brush type or brushless permanent magnet motors which are operated by direct current, the adjustment feature is most compatible with cordless clippers already using an on-board DC source in the form of a re-chargeable battery to drive the reciprocating blade. The invention will be described as a modification of a cordless clipper, although AC driven corded type clippers can also be modified with this feature by the addition of an on-board AC to DC power supply for the adjustment motor.

In the first embodiment, a modified blade set is used such that a gear rack is attached to the stationary blade. It is engaged with a worm gear pinion driven by a low speed gear motor through a reversible drive circuit. Either limit switches, limit sensors, or over-current sensors are used to disable the adjustment motor at either the long or short hair end limits. The motor then can only be driven in the opposite direction.

In the second embodiment, a conventional blade set is used. The modification is such that a motor-driven final gear replaces the manual handle thereby retaining the original mechanism (of any type) that is used to move the stationary blade relative to the reciprocating blade in the conventional blade set. A timing belt couples a rear mounted adjustment motor to a front side-mounted gear train coupled to the shaft of the blade shifting mechanism. Attached to the timing belt for linear back and forth excursions is a magnet with a pointer. The magnet is used to operate two normally closed magnetic reed switches placed at the opposite distal ends of the permissible excursion thereby serving the limit switch function. The pointer moves over a tri-colored linear scale viewable by the barber from the top of the hair clipper; this quickly indicates the hair length setting. A plastic housing cover over the adjustment motor at the back and over the timing belt and gear train at the side encloses the entire compact mechanism.

BRIEF DESCRIPTION OF THE DRAWINGS

The present invention can best be understood in connection with the accompanying drawings. It is noted that the invention is not limited to the precise embodiments shown in drawings, in which.

DETAILED DESCRIPTION OF THE INVENTION

Figure 1:
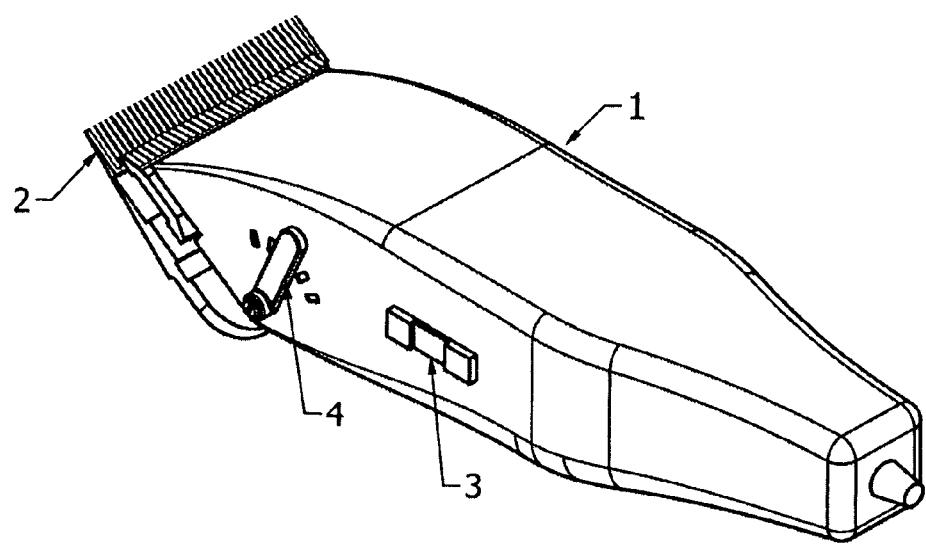
FIG. 1 is a perspective view of a typical prior art hair clipper with manual adjustment lever at the side.
Figure 2:
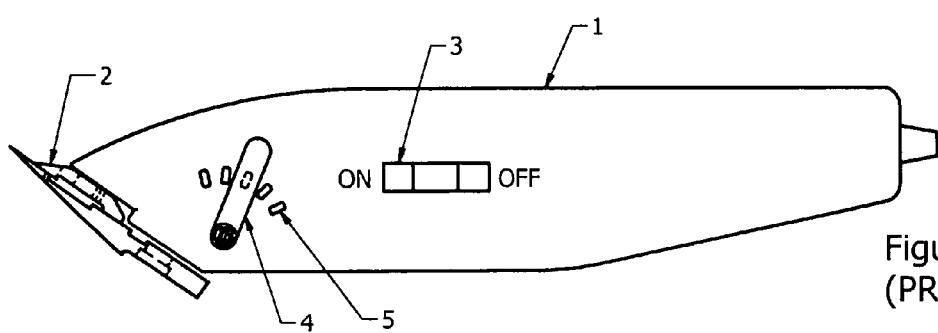
FIG. 2 is a side elevation of the prior art hair clippers of FIG. 1.

FIGS. 1 and 2 show two views of a conventional cordless electric hair clipper 1 with on/off switch 3, conventional blade set 2, and side manual incremental adjusting handle 4. The detents 5 engage handle 4 to set the minimum hair cutting length at one of the selections.

Figure 3:
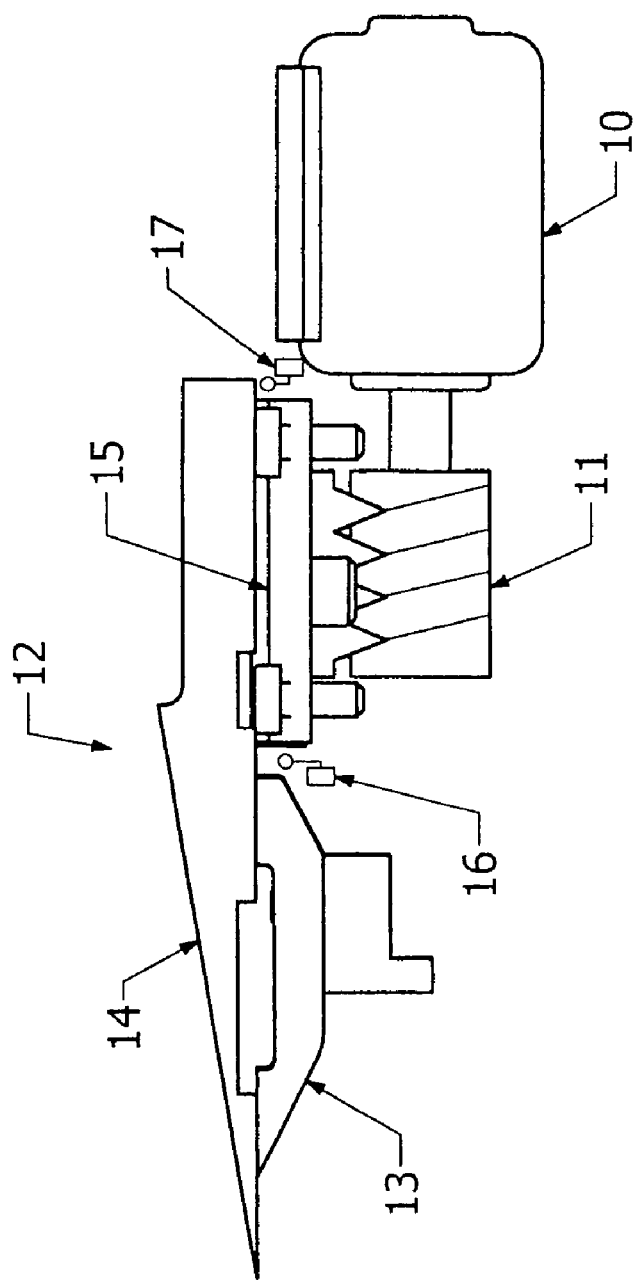
FIG. 3 is a side elevation of a motor-driven mechanism for adjusting the stationary blade of a clipper blade set showing a rack and worm gear pinion of the first embodiment.
Figure 4:
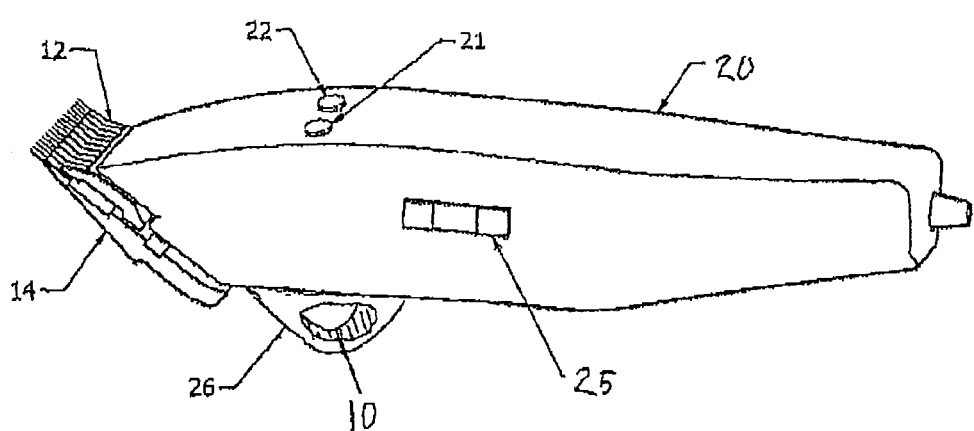
FIG. 4 is a perspective view of the hair clipper of this invention incorporating the mechanism of FIG. 3.
Figure 4A:
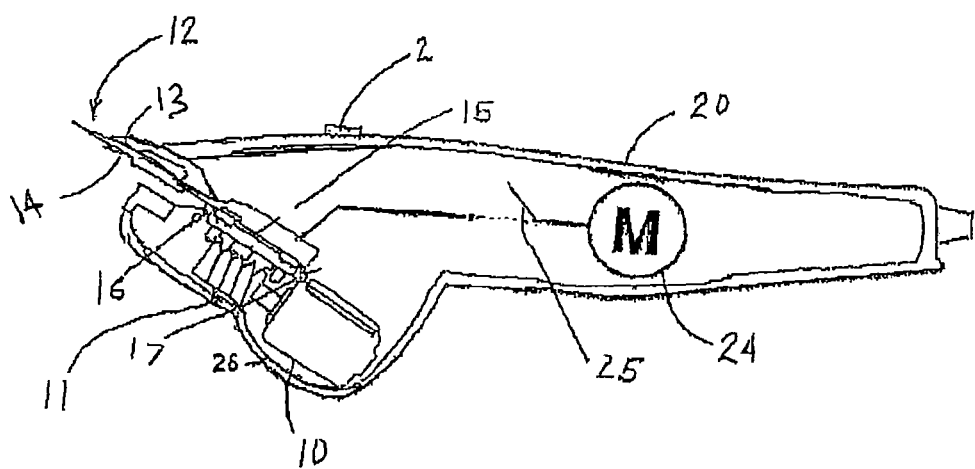
FIG. 4A is a side view in crossection of the hair clipper of this invention, showing the primary motor therein.

FIG. 3 shows the mechanism which uses gear motor 10 driving worm gear pinion 11 to perform an adjustment of stationary blade 14 relative to reciprocating blade 13 in blade set 12. A gear rack 15 subassembly is attached to blade 14 and engages pinion 11. Also shown in this view are limit switches 16 and 17 at the longest and shortest settings respectively. FIGS. 4 and 4A show clipper housing 20 with the adjustment feature. Conventional on/off switch 25 connected to clipper motor 24 (shown schematically as an encircled "M") is at one side while momentary (or "tap") switches 21 and 22 on the top surface are used to energize gearmotor 10 in a direction toward longer settings or shorter settings respectively. Gearmotor 10 is enclosed in descending housing 26, which descends below clipper housing 20. While FIGS. 3, 4 and 4A show a worm gear, it is anticipated that other gears may be used, such as rack and pinion gears or other gears known to those skilled in the art.

Figure 5:
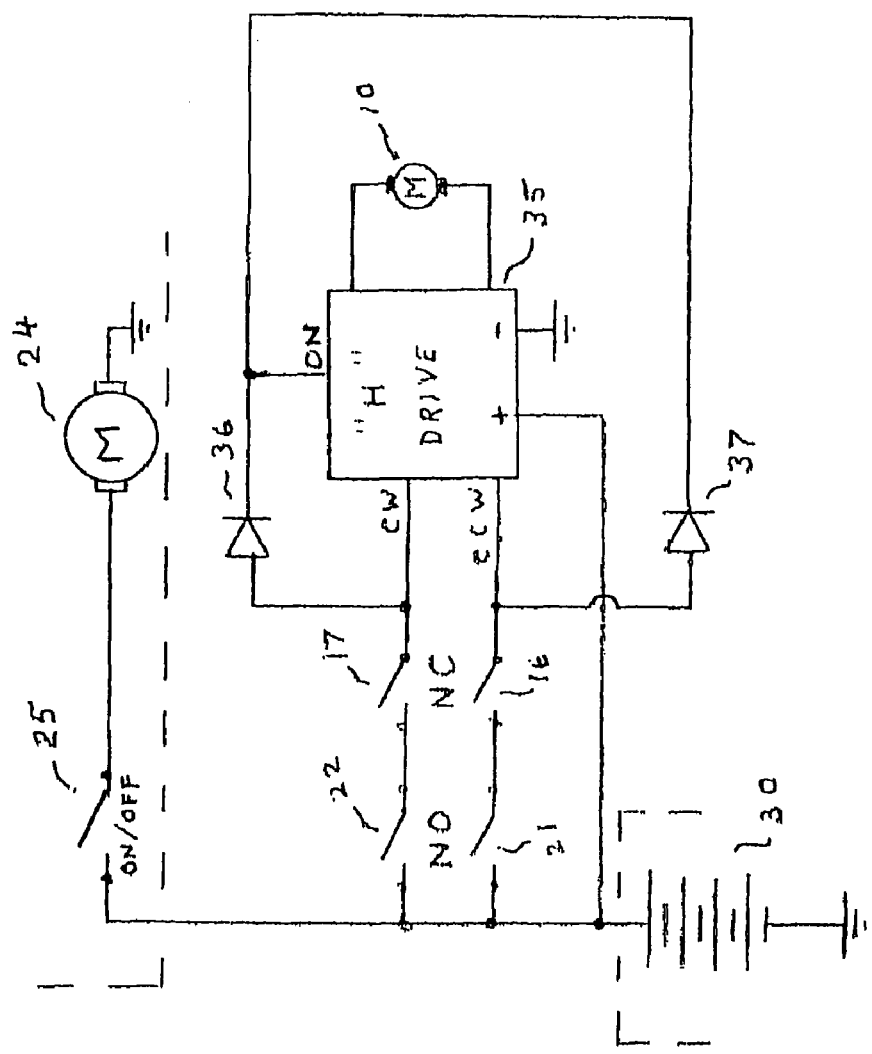
FIG. 5 is a wiring diagram of the adjustment motor using an "H-bridge" type of reversible driver.

FIG. 5 is a wiring diagram for the first embodiment of FIGS. 3 and 4 wherein gearmotor 10 is a simple brush type permanent magnet type driven by a common "H-bridge" drive module 35. Battery 30 is used primarily to power clipper motor 24 through on/off switch 25. It is also used as the power source for the adjustment feature. Drive module 35 has two direction inputs for clockwise and counter-clockwise operation, an "ON" input, and power input and motor output connections as shown. In operation, if normally open switch 22 is pushed, a signal will flow through normally closed limit switch 17 energizing the ON input through isolation diode 36; motor 10 will be driven clockwise until either switch 22 is released or limit switch 17 is opened at the end of the excursion. Similarly, if switch 21 is pushed, counter-clockwise operation is achieved through limit switch 16 and isolation diode 37. Once a limit switch is opened, motor 10 can only be driven in the opposite direction until the open limit switch is again closed.

Figure 6:
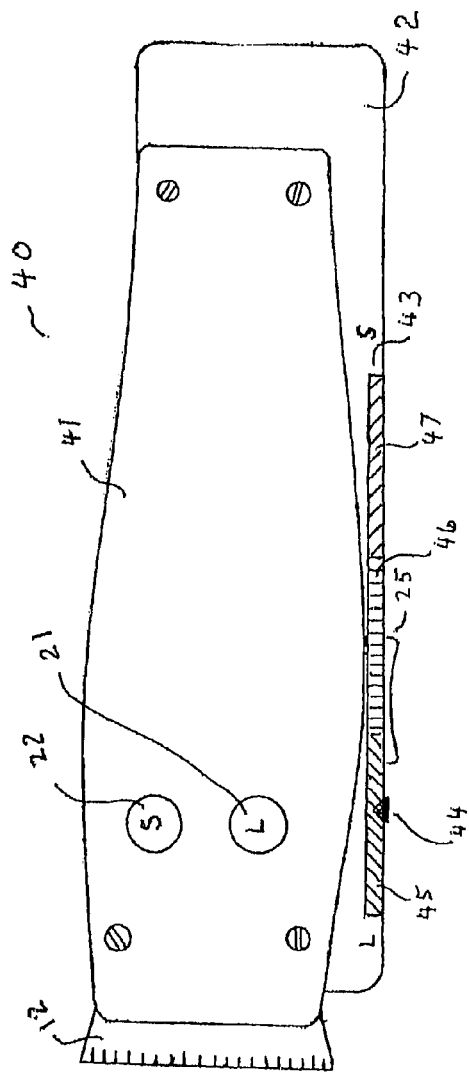
FIG. 6 is a top view of a second embodiment hair clipper with motor-driven adjustment of this invention.
Figure 7:
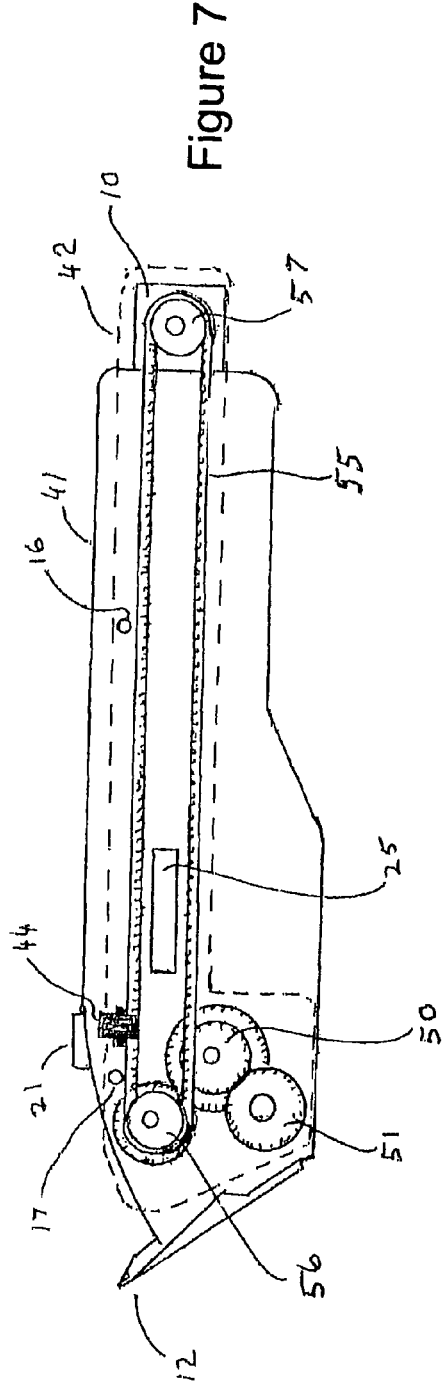
FIG. 7 is a side elevation of the second embodiment clipper with the housing cover removed to reveal the timing belt and gear train mechanism.

FIGS. 6 and 7 show top and side views of the second embodiment of motor-driven minimum hair length adjustable hair clippers. The same circuit shown in FIG. 5 is completely applicable to this embodiment as well. The same momentary ("tap") switches 21 and 22 are used to control motor 10 which is now placed at the back end of hair clipper 40. Except for the addition of switches 21 and 22, the housing 41 and internal mechanism is identical to that of the prior art cordless clipper shown in FIGS. 1 and 2. In this embodiment, a conventional blade set 12 and internal blade adjusting mechanism is used. The feature of this embodiment couples through the shaft formerly engaged with a manual handle 4. This is shown at the center of output gear 51. In the top view of FIG. 6, housing cover 42 is a plastic shell used to enclose the feature mechanism. In FIG. 7, this cover 42 is removed to reveal the mechanism; the position is shown in dashed lines. On the top edge of cover 42 is a tri-colored strip 43 with green region 45 denoting the long settings, yellow region 46 denoting medium length settings, and red region 47 denoting short settings. This scale is meant to be read relative to the position of pointer assembly 44 which is attached to timing belt 55 transmitting power and torque from pulley 57 mounted on motor 10 to pulley 56 attached to the input gear of gear train 50.

Gear train 50 is used to adjust the torque at output gear 51 and to match the speed and torque of gear motor 10 and the desired indicating excursion of belt 55 so as to form an ergonomic range. Besides the pointer on top, pointer assembly 44 also carries a small powerful magnet to operate limit switches 16 and 17 which are now implemented as normally closed magnetic reed switches. On/off switch 25 fits between timing belt 55 and pokes through a side switch hole in housing cover 42. While FIGS. 6 and 7 show a particular embodiment for an exterior mounted embodiment, it is anticipated that other exterior mounted embodiments may be used, such as those known to those skilled in the art.

In the foregoing description, certain terms and visual depictions are used to illustrate the preferred embodiment. However, no unnecessary limitations are to be construed by the terms used or illustrations depicted, beyond what is shown in the prior art, since the terms and illustrations are exemplary only, and are not meant to limit the scope of the present invention.

It is further known that other modifications may be made to the present invention, without departing the scope of the invention, as noted in the appended Claims.

I claim:

1. Hair clippers comprising:
   a clipper housing having forward and rear ends;
   a first motor encapsulated by said clipper housing and a reversible gearmotor drive system having a reversible gearmotor, said reversible gearmotor enclosed in a blade adjustment motor housing descending from said clipper housing;
   a length adjusting cutting blade extending from said forward end of said housing;
   a movable reciprocating cutting blade adjacent said length adjusting cutting blade spaced from said length adjusting cutting blade to establish a length of hair being cut, said movable reciprocating cutting blade being electrically driven by a first motor in said clipper housing;
   said length adjusting cutting blade movable longitudinally relative to said movable reciprocating blade which is reciprocated laterally in a transverse orthogonal direction relative to the adjustment movement of said length adjustment blade;
   said length adjusting cutting blade and said movable reciprocating blade each have a respective plurality of blade tips, wherein movement of said blade tips is adjusted, thereby allowing for different lengths of hair to be cut;
   said reversible gearmotor within said descending blade adjustment motor housing moves said length adjusting cutting blade relative to said movable reciprocating cutting blade to change the length of hair being cut;
   a pair of momentary tap switches on a top front mid portion of an outer surface of said clipper housing; said pair of momentary tap switches electrically connected to said reversible gearmotor drive system; to permit a user to adjust with one hand a position of said length adjusting cutting blade in said orthogonal direction to adjust the length of hair being cut, wherein one of said pair of momentary tap switches activates said gear motor to adjust the length adjusting cutting blade in one said orthogonal direction and the other one of said pair of momentary tap switches activates said gearmotor to adjust said length adjusting cutting blade in the other said orthogonal direction;
   said length of hair being cut being infinitely variable within a range of movement of said length adjusting cutting blade.

2. The hair clippers of claim 1 in which said gearmotor drive system comprises a gear rack subassembly engaged with said length adjusting cutting blade driven by said gearmotor within said descending blade adjustment motor housing.

3. The hair clippers of claim 2 in which said gearmotor drive system includes a pinion driven by said gearmotor, said pinion being engaged with said gear rack assembly.

4. The hair clippers of claim 3 having limit switches to limit movement of said length adjusting cutting blade.

5. The hair clippers of claim 4 in which said clipper housing has an on/off switch on a side wall.

6. The hair clippers of claim 5 in which said clipper housing contains a battery to power both said first motor driving said movable reciprocating cutting blades and said gearmotor in said descending housing driving said length adjusting cutting blade.

7. The hair clippers of claim 6 in which said battery is rechargeable.

8. The hair clippers of claim 1, wherein the first motor and the gearmotor are powered by a battery or by AC power.

9. The hair clippers of claim 1, wherein said gearmotor is a permanent magnet DC motor.

10. Hair clippers with electrically operated and adjustable blades comprising:
    a clipper housing with forward and rear ends;
    a length adjusting cutting blade extending from the forward end of said clipper housing;
    a first motor encapsulated by said clipper housing and a reversible gearmotor drive system having a reversible gearmotor, said reversible gear motor enclosed in a blade adjustment motor housing descending from said clipper housing;

a movable reciprocating cutting blade adjacent said length adjusting cutting blade spaced from said length adjusting cutting blade to establish a length of hair being cut, said reciprocating cutting blade being electrically driven by a first motor in said clipper housing;

said length adjusting cutting blade movable longitudinally relative to said movable reciprocating blade which is reciprocated laterally in a transverse orthogonal direction relative to the adjustment movement of said length adjustment blade;

said length adjusting cutting blade and said movable reciprocating blade each have a respective plurality of blade tips, wherein movement of said blade tips is adjusted, thereby allowing for different lengths of hair to be cut;

said reversible gearmotor located within said descending blade adjustment motor housing moves said length adjusting cutting blade relative to said movable reciprocating cutting blade to change the length of hair being cut; and, a pair of momentary tap switches on a top outer surface of said clipper housing; said pair of momentary tap switches electrically connected to said reversible gearmotor drive system to permit a user to adjust with one hand a position of said length adjusting cutting blade in said orthogonal direction in either said orthogonal direction to adjust the length of hair being cut, said length of hair being cut being infinitely variable within a range of movement of said length adjusting cutting blade;

said length of hair being cut being infinitely variable within a range of movement of said length adjusting cutting blade.

* * * * *